United States Patent
Ritter et al.

(10) Patent No.: US 11,197,848 B2
(45) Date of Patent: Dec. 14, 2021

(54) TOPICAL AMLODIPINE SALTS FOR THE TREATMENT OF ANORECTAL DISEASES

(71) Applicant: Tavanta Therapeutics Hungary Incorporated, Budapest (HU)

(72) Inventors: László Ritter, Budapest (HU); László Hornok, Nagykovácsi (HU); Péter Mátyus, Budapest (HU); Romána Zelkó, Budapest (HU); Andrea Ujhelyi, Nyiregyhaza (HU); Richárd Balázs Kárpáti, Tatabánya (HU); Tamás Solymosi, Békéscsaba (HU); Hristos Glavinas, Szeged (HU)

(73) Assignee: TAVANTA THERAPEUTICS HUNGARY INCORPORATED

( * ) Notice: Subject to any disclaimer, the term of this patent is extended or adjusted under 35 U.S.C. 154(b) by 0 days.

(21) Appl. No.: 16/425,028

(22) Filed: May 29, 2019

(65) Prior Publication Data
US 2019/0365732 A1   Dec. 5, 2019

Related U.S. Application Data

(60) Provisional application No. 62/822,400, filed on Mar. 22, 2019, provisional application No. 62/679,137, filed on Jun. 1, 2018.

(51) Int. Cl.
*A61K 31/4422* (2006.01)
*A61K 9/00* (2006.01)
*A61K 47/36* (2006.01)

(52) U.S. Cl.
CPC ........ *A61K 31/4422* (2013.01); *A61K 9/0014* (2013.01)

(58) Field of Classification Search
None
See application file for complete search history.

(56) References Cited

U.S. PATENT DOCUMENTS

| | | | | |
|---|---|---|---|---|
| 6,544,530 B1 | * | 4/2003 | Friedman | A61K 8/06 424/400 |
| 2010/0010052 A1 | | 1/2010 | Engblom | |
| 2010/0183519 A1 | * | 7/2010 | Katz | A61K 9/0014 424/9.2 |
| 2011/0207765 A1 | * | 8/2011 | Van Den Bussche | A61K 9/06 514/292 |
| 2016/0129091 A1 | * | 5/2016 | Twidwell | A61K 45/06 424/85.7 |

FOREIGN PATENT DOCUMENTS

| | | |
|---|---|---|
| EP | 331382 | 9/1989 |
| WO | WO1999018957 A1 * | 4/1999 |
| WO | 2019229535 | 12/2019 |

OTHER PUBLICATIONS

Lane ME. Skin penetration enhancers. International journal of pharmaceutics. Apr. 15, 2013;447(1-2):12-21. (Year: 2013).*
Soap and Detergent Association. Glycerine: an overview. Terms, Technical Data, Properties, Performance. 1990. (Year: 1990).*
International Application No. PCT/IB2019/000689; International Search Report and Written Opinion of the International Searching Authority, dated Dec. 19, 2019; 12 pages.
International Application No. PCT/IB2019/000689; International Preliminary Report on Patentability, dated Dec. 10, 2020; 9 pages.

\* cited by examiner

*Primary Examiner* — Nissa M Westerberg
(74) *Attorney, Agent, or Firm* — Saliwanchik, Lloyd & Eisenschenk

(57) ABSTRACT

Provided is a topical pharmaceutical gel composition of an amlodipine salt and methods for its use in the treatment of anorectal disease.

6 Claims, 1 Drawing Sheet

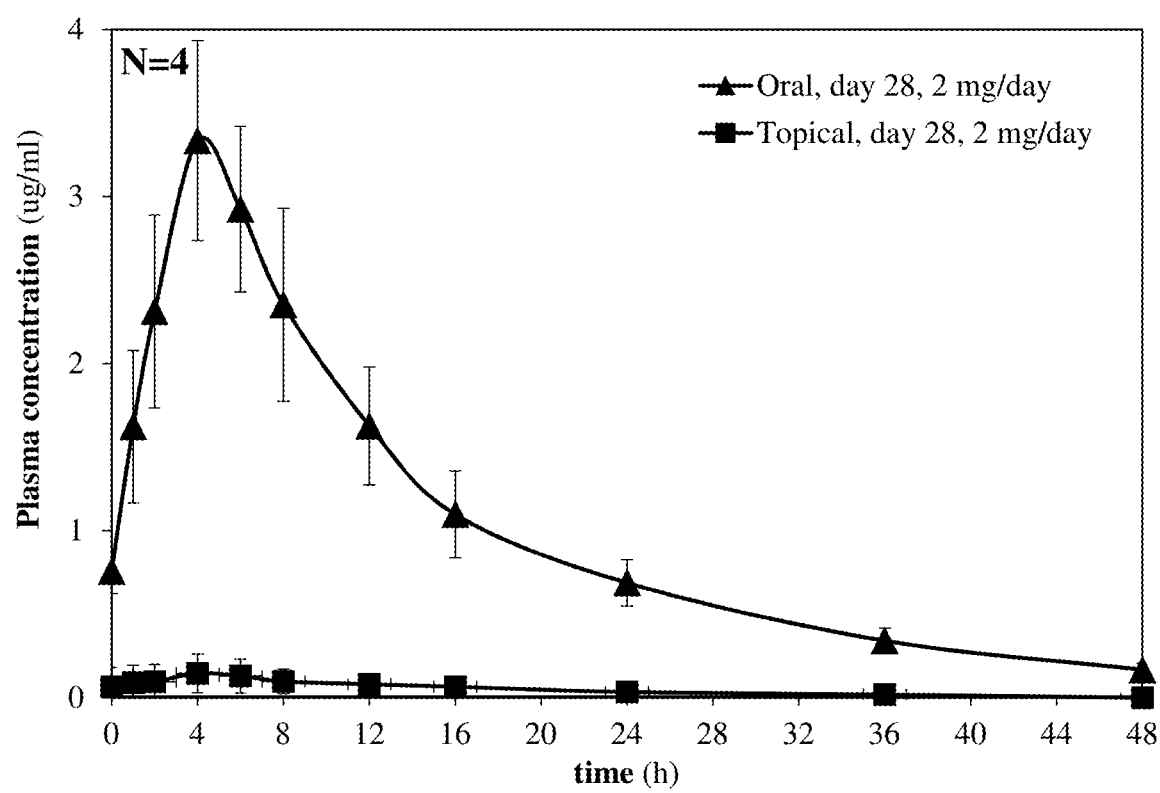

TOPICAL AMLODIPINE SALTS FOR THE TREATMENT OF ANORECTAL DISEASES

The present disclosure relates to topical pharmaceutical gel compositions containing amlodipine salts. Topical pharmaceutical gel compositions containing amlodipine salts are suited for use in treating anorectal diseases such as hemorrhoids, anal fissure (acute and chronic), painful conditions after anorectal surgery, perianal abscess, prolapsed thrombosed piles, perianal haematoma, cancer invading the sphincters (anorectal cancer), anal herpes, anal warts, anal itching, proctalgia fugax, constipation, anal bleeding and Crohn's disease or another inflammatory bowel disease related anorectal disorders.

Anorectal disease refers to ailments of the anus and/or rectum. The most common conditions include hemorrhoids, anal warts, anal fissures, anorectal abscesses and anal fistulas.

Hemorrhoids develop when tissues of the rectum and anus become swollen and inflamed. Hemorrhoids can be located inside the anus (internal hemorrhoids) or in the area surrounding the anus (external). Symptoms include pain, inflammation and itching.

Treatment for mild cases of hemorrhoids may include sitz baths, cool compresses, pain relievers and over-the-counter topical medication. For chronic hemorrhoids, there are several options such as hemorrhoid banding, injections and infrared coagulation. Surgical options such as hemorrhoidectomy and stapling are reserved for the most serious cases.

Condyloma, or anal warts, are caused by the human papilloma virus (HPV) and form on the skin around the anus. There are many types of papilloma virus. Some types develop warts on the hands and feet while others cause genital and anal warts. Many people do not complain of any complications from anal warts. Others complain of itching, bleeding or moisture in the anal area.

Treatment for anal warts include cauterization, ointments or a special type of acid (podophyllin or bichloracetic acid). Several treatments are necessary to cure anal warts. Even if the warts have been "removed," the virus can remain in the skin tissues. Follow-up visits are necessary for several months.

Anal fissures are small tears in the lining of the anus. These tears can be caused by hard, dry bowel movements, diarrhea and inflammation. Symptoms include itching, pain and bleeding.

The anal fissure is acute when it heals with 4-8 weeks of conservative therapy. If this therapy fails and the fissure becomes chronic (S. Schlichtemeier, A. Engel, *Aust Prescr,* 2016, 39, pp 14).

Overall incidence of anal fissure is of 1.1 per 1000 person-years translates to an average life time risk of 7.8. Approximately 40% of patients develop chronic anal fissure.

The pathophysiology of anal fissures is not entirely clear and understood. A widely accepted scientific explanation (M. H. Madalinski, *World J Gastrointest Pharmacol Ther,* 2011, 2(2), pp 9; M. M. van Meegdenburg, M. Trzpis, E Heineman, P. M. A. Broens, *Medical Hypotheses,* 2016, 94, pp 25; M. van Outryve, *Acta Chirurgica Belgica,* 2006, 106(5), pp 517) is that an acute injury leads to local pain and spasm of the internal anal sphincter. This spasm and the resulting high resting anal sphincter pressure leads to reduced blood flow and ischaemia and poor healing. Unless this cycle is broken the fissure will persist or become chronic fissure.

Clinicians agree that a constantly elevated rest pressure in the anal sphincter plays a crucial role in the pathogenesis of anal fissures. Schouten et. al. (W. R. Schouten, J. W. Briel, J. J. Auwerda, *Dis Colon Rectum,* 1994, 37, pp 664) showed that the anodermal blood flow rates correlated inversely with the anal resting pressures measured by Doppler laser flowmetry and anorectal manometry, respectively. The increased pressure resulted in a lowered blood flow. Patients with fissures had high resting pressures and also low perfusion rates. This low perfusion can be attributed to the scarcity of small arteriolar anastomoses between the end branches of the left and right inferior rectal arteries dorsally. Fissures generate in this region, when the resting sphincter pressure is sufficiently higher than the pressure in the small arterioles. Chronic anal fissures can therefore be considered as ischemic ulcers. Moreover Maria et. al. (G. Maria, D. Brisinda, M. P. Ruggieru, et al. *Surgery,* 1999, 126, pp 535) demonstrated antiendothelial antibodies in patients with an anal fissure, not in controls. These antibodies activate the endothelium, generating vasoconstriction and procoagulant activity. This mechanism also induces ischemia of the anoderm and the formation of a fissure. The end stage of the fissure as an ischemic ulcer is a fibrotic lesion with a concomitant hypertrophic papilla and sentinel skin tag. Fibrosis is an important obstacle to healing and can result in an atonic ulcer. Chronic inflammation of the fissure can also provoke a local abscess and fistulisation.

The majority of acute fissures resolve with the aid of topical local anesthetics and stool softeners. Moreover, a proportion go on to become chronic. Whatever their cause, it is known that they are associated with an increased resting tone. Treatment for fissures has therefore been targeted at reducing resting anal pressure, which in turn results in an increased blood flow to the posterior commissure and healing of the fissure.

The traditional treatment to reduce tone in the anal sphincter has been the anal dilatation in which 4 fingers are gradually inserted into the anus under deep general anesthesia and gently separated thus breaking the fibers of the internal sphincter in a radial fashion. The risks to continence of this approach are obvious and have been estimated at 30% for temporary incontinence and up to a 10% risk of permanent fecal incontinence. It has consequently fallen out of favor with most surgeons. The preferred procedure is the lateral internal sphincterotomy, which can be performed by either an open or closed technique.

Although lateral sphincterotomy has become the gold standard for the treatment of anal fissures, these complications have driven the search for other methods of reducing anal pressure. Research has been directed towards finding a means of pharmacologically reducing anal pressure whilst leaving the ring of internal anal sphincter muscle intact.

Chemical sphincterotomy has been tried using a variety of novel agents including topical GTN, calcium channel blockers such as nifedipine or diltiazem and botulinum toxin. Some of these agents were found to be effective in healing chronic anal fissure with negligible side effects and are now considered as first line treatment for chronic anal fissure.

Only glyceryl trinitrate (GTN) ointment is approved for the treatment of moderate to severe pain associated with chronic anal fissure. In three Phase 3 studies conducted and submitted to the regulatory bodies worldwide, healing of anal fissures in patients treated with Rectogesic 4 mg/g Rectal Ointment was not statistically different from placebo (Public assessment report, UK/H/0823/001/MR). Severe headaches caused by application of GTN resulted in 30% of the patient to discontinuing its use. Various concentrations of GTN has been tested but 0.2% dosing (×2-3 daily) offers the same healing rate as with higher concentrations but with a lower incidence of headache. The best way to minimize and/or eliminate headaches is to apply the GTN on the anal area in recumbent position. An immediate rush or heat is felt in the head caused by vasodilatation of cerebral vessels which subsides just as quickly. The patient then can get up and resume normal activity. Application of GTN in the anal canal is unnecessary and causes undue pain as its mode of action is through absorption from the skin (such as nitropaste for treatment of angina pectoris). Application of GTN in a hurry and in sitting or standing portion increases the incidence of headaches (6% v 56%) and may result in premature discontinuation of treatment (A. M. Abcarian, H. Abcarian, *Internal Medicine Review*, 2018, 4(1), pp 1).

CCBs have been used for many years in coronary heart disease because blockade of the calcium channel produces smooth muscle relaxation in the arteriolar wall. Several studies suggest that topical CCBs are as effective as GTN and have fewer side effects (K. N. Zaghyian and P. Fleshner, *Clin Colon Rectal Surg*, 2011, 24, pp 22). Despite of the use of CCBs in the treatment of chronic anal fissure, approved product containing CCBs is available on the market. In other cases, only compounded creams or ointments containing CCBs can be used for the treatment. Compounded drugs have several drawbacks, such as limited number of compounding pharmacies, Physicians has to write a "recipe" for the compounded CCBs (off-label use), and concentration of compounded drugs is highly variable between pharmacies, prescriptions and within each tubes and lack of reimbursement.

CCBs reduce the amount of calcium entering cells of the heart and blood vessel walls. Calcium passes into these cells through the ion channels. These channels are blocked by CCBs, thereby reducing the amount of calcium entering cells of the heart and blood vessel walls. As a result, the blood vessels relax, and the heart muscle receives more oxygenated blood, which is how CCBs are able to lower blood pressure and treat angina. Some CCBs also block calcium going into the conducting cells in the heart and have the added effect of slowing the heart rate.

There are two distinct chemical classes of CCBs: the dihydropyridines (such as nifedipine and amlodipine) and the nondihydropyridines (diltiazem and verapamil). The two classes both help to relax and widen arteries but non-dihydropyridines have an additional effect on the heart's conduction system and can help to control certain fast heart rhythms (such as atrial fibrillation). This is because non-dihydropyridines also block calcium going into the conducting cells in the heart, which has the effect of slowing down the heart rate.

Targeting the internal anal sphincter with topically applied amlodipine salts relies on the effective transcutaneous flux of drug substance.

There is a significant and very long-standing need to identify agents which can be applied topically to treat anorectal diseases, and which have favorable benefit to risk rations. Optimally such agents should primarily act locally, and systemic absorption should not result in blood levels high enough to cause significant systemic effect or toxicity.

SUMMARY

Provided is a composition for the topical treatment of anorectal diseases, containing a therapeutic amount of a calcium channel blocker, such as an amlodipine salt.

Also provided is a composition for the topical treatment of anorectal diseases prepared by a method comprising dissolving or suspending a calcium channel blocker, such as an amlodipine salt, in an appropriate preparation for topical administration. Also provided is a topical pharmaceutical gel composition comprising an amlodipine salt and a carrier.

Also provided is a method and composition for the topical treatment of anorectal diseases that limits significant systemic effects and reduces the occurrence of adverse events caused by the current approved therapies.

Also provided is a topical pharmaceutical gel composition for treating anorectal diseases such as hemorrhoids, anal fissure (acute and chronic), painful conditions after anorectal surgery, perianal abscess, prolapsed thrombosed piles, perianal haematoma, cancer invading the sphincters (anorectal cancer), anal herpes, anal warts, anal itching, proctalgia fugax, constipation, anal bleeding and Crohn's disease or another inflammatory bowel disease related anorectal disorders.

Also provided is a topical pharmaceutical gel composition of an amlodipine salt comprising:
  about 0.01-1% w/w of an amlodipine salt, as measured as the free base;
  about 5-75 w/w of at least one glycol solvent;
  about 0.1-10% w/w of at least one gelling agent;
  about 0.001-5 w/w of at least one preservative;
  about 5-75% w/w of glycerin;
  about 1-20% w/w of ethanol; and
  about 10-40% w/w of water.

Also provided is a topical pharmaceutical gel composition of amlodipine besylate comprising:
  about 0.01-1% w/w of amlodipine besylate, as measured as the free base;
  about 5-75 w/w of at least one glycol solvent;
  about 0.1-10% w/w of hydroxyethyl cellulose;
  about 5-75% w/w of glycerin;
  about 1-20% w/w of ethanol; and
  about 10-40% w/w of water.

Also provided is a topical pharmaceutical gel composition of amlodipine besylate comprising:
  about 0.01-1% w/w of amlodipine besylate, as measured as the free base;
  about 5-75 w/w of propylene glycol;
  about 0.1-10% w/w of at least one gelling agent;
  about 5-75% w/w of glycerin;
  about 1-20% w/w of ethanol; and
  about 10-40% w/w of water.

Also provided is a topical pharmaceutical gel composition of amlodipine besylate comprising:
  about 0.01-1% w/w of amlodipine besylate, as measured as the free base;
  about 5-75 w/w of propylene glycol;
  about 0.1-10% w/w of hydroxyethyl cellulose;
  about 0.01-5% w/w of methyl parahydroxybenzoate;
  about 5-75% w/w of glycerin;
  about 1-20 w/w of ethanol; and
  about 10-40% w/w of water.

Also provided is a method for the treatment of an anorectal disease comprising topically applying a topical pharmaceutical gel composition described herein to a skin surface of a patient in need thereof.

These and other aspects of the invention will be apparent upon reference to the following detailed description. To this end, all publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIGURE" and "FIG." herein) of which:

The FIGURE shows the mean±SD plasma level curves for amlodipine in female Göttingen minipigs on day 28 when administered orally (Oral) or topically as 0.2% topical pharmaceutical gel (Topical).

DESCRIPTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" or "some embodiments" or "a certain embodiment" means that a particular feature, structure or characteristic described in connection with the embodiment is included in at least one embodiment. Thus, the appearances of the phrases "in one embodiment" or "in an embodiment" or "in some embodiments" or "in a certain embodiment" in various places throughout this specification are not necessarily all referring to the same embodiment. Furthermore, the particular features, structures, or characteristics may be combined in any suitable manner in one or more embodiments.

Amlodipine is a dihydropyridine calcium antagonist that inhibits the transmembrane influx of calcium ions into vascular smooth muscle and cardiac muscle. Experimental data suggest that amlodipine binds to both dihydropyridine and nondihydropyridine binding sites. The contractile processes of cardiac muscle and vascular smooth muscle are dependent upon the movement of extracellular calcium ions into these cells through specific ion channels. Amlodipine inhibits calcium ion influx across cell membranes selectively, with a greater effect on vascular smooth muscle cells than on cardiac muscle cells. Negative inotropic effects can be detected in vitro but such effects have not been seen in intact animals at therapeutic doses. Serum calcium concentration is not affected by amlodipine. Within the physiologic pH range, amlodipine is an ionized compound (pKa=8.6), and its kinetic interaction with the calcium channel receptor is characterized by a gradual rate of association and dissociation with the receptor binding site, resulting in a gradual onset of effect.

Amlodipine is a peripheral arterial vasodilator that acts directly on vascular smooth muscle to cause a reduction in peripheral vascular resistance and reduction in blood pressure.

Following administration of therapeutic doses to patients with hypertension, amlodipine produces vasodilation resulting in a reduction of supine and standing blood pressures. These decreases in blood pressure are not accompanied by a significant change in heart rate or plasma catecholamine levels with chronic dosing. Although the acute intravenous administration of amlodipine decreases arterial blood pressure and increases heart rate in hemodynamic studies of patients with chronic stable angina, chronic oral administration of amlodipine in clinical trials did not lead to clinically significant changes in heart rate or blood pressures in normotensive patients with angina.

With chronic once daily oral administration, antihypertensive effectiveness is maintained for at least 24 hours. Plasma concentrations correlate with effect in both young and elderly patients. The magnitude of reduction in blood pressure with amlodipine is also correlated with the height of pretreatment elevation; thus, individuals with moderate hypertension (diastolic pressure 105-114 mmHg) had about a 50% greater response than patients with mild hypertension (diastolic pressure 90-104 mmHg). Normotensive subjects experienced no clinically significant change in blood pressures (+1/−2 mmHg).

Amlodipine does not change sinoatrial nodal function or atrioventricular conduction in intact animals or man. In patients with chronic stable angina, intravenous administration of 10 mg did not significantly alter A-H and H-V conduction and sinus node recovery time after pacing. Similar results were obtained in patients receiving amlodipine and concomitant beta-blockers. In clinical studies in which amlodipine was administered in combination with beta-blockers to patients with either hypertension or angina, no adverse effects on electrocardiographic parameters were observed. In clinical trials with angina patients alone, amlodipine therapy did not alter electrocardiographic intervals or produce higher degrees of AV blocks.

After oral administration of therapeutic doses of amlodipine, absorption produces peak plasma concentrations between 6 and 12 hours. Absolute bioavailability has been estimated to be between 64 and 90%. The bioavailability of amlodipine is not altered by the presence of food.

Amlodipine is extensively (about 90%) converted to inactive metabolites via hepatic metabolism with 10% of the parent compound and 60% of the metabolites excreted in the urine. Ex vivo studies have shown that approximately 93% of the circulating drug is bound to plasma proteins in hypertensive patients Elimination from the plasma is biphasic with a terminal elimination half-life of about 30-50 hours. Steady-state plasma levels of amlodipine are reached after 7 to 8 days of consecutive daily dosing.

The pharmacokinetics of amlodipine are not significantly influenced by renal impairment. Patients with renal failure may therefore receive the usual initial dose.

Elderly patients and patients with hepatic insufficiency have decreased clearance of amlodipine with a resulting increase in AUC of approximately 40-60%, and a lower initial dose may be required. A similar increase in AUC was observed in patients with moderate to severe heart failure Amlodipine is indicated for the treatment of hypertension to lower blood pressure, symptomatic treatment of chronic stable angina, confirmed or suspected vasospastic angina and to reduce the risk of hospitalization for angina and to reduce the risk of a coronary revascularization procedure.

The usual initial antihypertensive oral dose of Amlodipine is 5 mg once daily, and the maximum dose is 10 mg once daily. The recommended dose for chronic stable or vasospastic angina is 5-10 mg, with the lower dose suggested in the elderly and in patients with hepatic insufficiency. Most patients will require 10 mg for adequate effect. The effective antihypertensive oral dose in pediatric patients ages 6-17 years is 2.5 mg to 5 mg once daily. Doses in excess of 5 mg daily have not been studied in pediatric patients.

As used herein, "amlodipine salt" refers to an acid addition salt of amlodipine. Acid addition salts may be prepared by methods well known in the art, and may be formed from organic and inorganic acids. Suitable acids include 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (-L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (-L), salicylic acid, sebacic acid, stearic acid, succinic acid, sulfuric acid, tartaric acid (+L), thiocyanic acid, toluenesulfonic acid (p), and undecylenic acid.

Also, as used in this specification and the appended claims, the singular forms "a," "an," and "the" include plural referents unless the content clearly dictates otherwise.

As used herein, "amlodipine besylate" may be referred to as 3-ethyl-5-methyl (±)-2-[(2-aminoethoxy)methyl]-4-(2-chlorophenyl)-1,4-dihydro-6-methyl-3,5-pyridinedicarboxylate, monobenzenesulphonate. Its empirical formula is $C_{20}H_{25}ClN_2O_5 \cdot C_6H_6O_3S$, and its structural formula is:

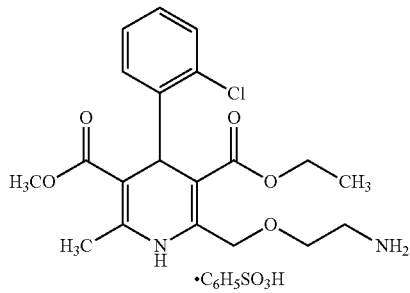 [SMILES: "·C6H5SO3H" ; CCOC(=O)C1=C(COCCN)NC(C)=C(C(=O)OC)C1c1ccccc1Cl]

Amlodipine besylate is a white crystalline powder with a molecular weight of 567.1. It is slightly soluble in water and sparingly soluble in ethanol. Amlodipine besylate tablets are formulated as white tablets equivalent to 2.5, 5, and 10 mg of amlodipine for oral administration. In addition to the active ingredient, amlodipine besylate, each tablet contains the following inactive ingredients: microcrystalline cellulose, dibasic calcium phosphate anhydrous, sodium starch glycolate, and magnesium stearate. Amlodipine besylate is instable in aqueous solution. Various attempts were made in order to develop orally available liquid formulations (M. Friciu et. al. *CJHP*, 2016, 69(4), pp 327; I. Kasagić Vujanović, et. al., *Contemporary Materials*, 2014, V-2 (2014), pp 214; Z. . Stoiljkovi☐ et. al., *Chem. Ind. Chem. Eng. Q.*, 2014, 20(2) pp 295; C. Milap et. al., Nahata, *J Am Pharm Assoc.*, 1999, 39, pp 375; A. Abdoh et. al., Pharm. Dev. Tecnol., 2004, 9(1), pp. 15), however stable liquid based formulations have not been developed to date.

There has been work done on the development of transdermal systems for calcium channel antagonists (Zeng, et al., *Drug Development and Industrial Pharmacy*, 2010, 36(6), pp 724; Y. Jiang, et al., *Pharmazie*, 2008, 63, pp 356; Patel, et al., *Asian Journal of Pharmaceutical and Clinical Research*, 2010, 3(1), pp 31). McDaid et. al. (*International Journal of Pharmaceutics*, 1996, 133, pp 71) investigated the topical absorption of amlodipine besylate and confirmed that the compound was too hydrophilic for adequate transdermal delivery using a convenient area of device, despite the use of penetration enhancers and increase in the thermodynamic gradient across various rate-controlling membranes by ethanol. Permeation of amlodipine from a range of hydrophilic and hydrophobic bases through hairless mouse skin was studied and the influence of the penetration enhancers, sodium lauryl sulphate 1% and propylene glycol 20% in a sodium carboxymethylcellulose 3% gel base was examined. In vivo studies using rabbits were performed to assess the suitability of a reservoir-type device. Employing data obtained from in vitro studies involving human abdominal skin, it was possible to predict the plasma profile resulting from the application of a similar device onto human skin over a period of 1 week and was found to be inadequate for clinical use. No adverse local effects in the animal model arising from the application of the transdermal device were observed. The therapeutic plasma level of amlodipine was in the range 3-10 ng/ml. The average absorption rate of 1.24 $\mu g/cm^2$ per h would result in a daily dose of 0.59 mg amlodipine being delivered using an exposure area of 20 $cm^2$. This dosage falls short of the desired level of ~3.2 mg. Both application sites in rabbits were examined visually for signs of local irritation after wearing the device for 3 days. No local irritation was observed at either application site, confirming that the device was well tolerated on dermal application even after several days of wear. These results are not surprising as the $Ca^{2+}$ antagonists inhibition activity in acute and chronic models of inflammation in a dose-dependent manner is widely known.

The subject invention is based on the discovery that anorectal diseases can be treated by topical formulations comprising a calcium channel blocker, such as amlodipine salts. Moreover, this treatment can be directed to the site of application and immediate surrounding area without a significant similar systemic effect.

Provided is a topical pharmaceutical gel composition comprising an amlodipine salt and a carrier.

In one aspect, the topical pharmaceutical gel compositions comprise an amlodipine salt and a carrier, with an amlodipine salt present at a concentration chosen from about 1% w/w, about 0.5% w/w, about 0.2% w/w, about 0.1% w/w, about 0.05% w/w and 0.01% w/w, as measured as the free base.

In an embodiment, the carrier comprises at least one glycol solvent, at least one gelling agent, and at least one diluent.

In an embodiment, the carrier further comprises one or more components chosen from preservatives and antioxidants.

In an embodiment, the carrier comprises one or more components chosen from hydroxyethyl cellulose, methyl parahydroxybenzoate, ethanol, water, propylene glycol, and glycerin.

Also provided is a topical pharmaceutical gel composition of an amlodipine salt comprising:
about 0.01-1% w/w of an amlodipine salt, as measured as the free base;
about 5-75 w/w of at least one glycol solvent;
about 0.1-10% w/w of at least one gelling agent; and
about 0.001-5 w/w of at least one preservative.

Also provided is a topical pharmaceutical gel composition of an amlodipine salt comprising:
about 0.01-1% w/w of an amlodipine salt, as measured as the free base;
about 5-75 w/w of at least one glycol solvent;
about 0.1-10% w/w of at least one gelling agent;
about 0.001-5% w/w of at least one preservative; and
at least one diluent.

In an embodiment, the amlodipine salt is chosen from amlodipine besylate, amlodipine maleate, amlodipine mesylate, amlodipine adipate, amlodipine camsylate and amlodipine nicotinate. In an embodiment, the amlodipine salt is chosen from amlodipine besylate, amlodipine maleate, and amlodipine mesylate. In an embodiment, the amlodipine salt is amlodipine besylate.

In an embodiment, the amlodipine salt is present at a concentration chosen from about 0.01% w/w to about 1% w/w, as measured as the free base. In an embodiment, the amlodipine salt is present at a concentration chosen from about 1% w/w, about 0.5% w/w, about 0.2% w/w, about 0.1% w/w, about 0.05% w/w and 0.01% w/w, as measured as the free base.

In an embodiment, the at least one glycol solvent is chosen from propylene glycol, polyethylene glycol, ethylene glycol, butylene glycol, hexalylene glycol, and mixtures thereof.

In an embodiment, the glycol solvent is polyethylene glycol.

In an embodiment, the at least one glycol solvent is present in an amount of about 5-75% w/w. In an embodiment, the at least one glycol solvent is present in an amount of about 5-50% w/w. In an embodiment, the at least one glycol solvent is present in an amount of about 10-40% w/w. In an embodiment, the at least one glycol solvent is present in an amount of about 15-30% w/w, such as about 20-30% w/w, for example about 25% w/w.

In an embodiment, the at least one gelling agent is chosen from carbomers, xanthan gum, acacia, tragacanth, sodium alginate, gelatin, modified starches, hydroxypropyl cellulose, hydroxyethyl cellulose, hydroxypropyl methylcellulose, carboxymethyl cellulose, carboxymethyl cellulose sodium, hydroxypropyl methylcellulose phthalate, methyl cellulose, co-polymers formed between maleic anhydride and methyl vinyl ether, methacrylate derivatives, polyethylene oxides, polyoxyethylene-polyoxypropylene copolymers, polyvinyl alcohol and mixtures thereof.

In an embodiment, the at least one gelling agent is chosen from carbomers, xanthan gum, acacia, tragacanth, sodium alginate, gelatin, modified starches, hydroxypropyl cellulose, hydroxyethyl cellulose, hydroxypropyl methylcellulose, hydroxypropyl methylcellulose phthalate, methyl cellulose, carboxymethyl cellulose, co-polymers formed between maleic anhydride and methyl vinyl ether, methacrylate derivatives, polyethylene oxides, polyoxyethylene-polyoxypropylene copolymers, polyvinyl alcohol and mixtures thereof.

In an embodiment, the gelling agent is hydroxyethyl cellulose.

In an embodiment, the at least one gelling agent is present in an amount of about 0.1-10% w/w. In an embodiment, the at least one gelling agent is present in an amount of about 0.1-5% w/w. In an embodiment, the at least one gelling agent is present in an amount of about 1-% w/w. In an embodiment, the at least one gelling agent is present in an amount of about 1-4% w/w. In an embodiment, the at least one gelling agent is present in an amount of about 1, about 2, about 3, or about 4% w/w.

In an embodiment, the at least one preservative is chosen from methyl paraben, propyl paraben, chlorocresol, thomersal, sorbic acid, potassium sorbate, methyl parahydroxybenzoate and mixtures thereof.

In an embodiment, the preservative is methyl parahydroxybenzoate.

In an embodiment, the preservative is present in an amount of about 0.001-5% w/w. In an embodiment, the preservative is present in an amount of about 0.001-1% w/w. In an embodiment, the preservative is present in an amount of about 0.001-0.005% w/w, such as about 0.001, about 0.002, about 0.003, about 0.004, or about 0.005% w/w.

In an embodiment, the topical pharmaceutical gel composition further comprises at least one diluent.

In an embodiment, the at least one diluent is chosen from ethanol, propanol, 2-propanol, water, glycerin, and mixtures thereof.

In an embodiment, the at least one diluent comprises about 5-75% w/w of glycerin, such as about 5-70% w/w, about 5-65% w/w, about 5-60% w/w, about 5-55% w/w, about 5-50% w/w, about 5-45% % w/w, or about 4-40% w/w.

In an embodiment, the at least one diluent comprises about 1-20% w/w of ethanol, such as about 1-15% w/w or about 5-15% w/w, for example, about 5, about 6, about 7, about 8, about 9, about 10, about 11, about 12, about 13, about 14, or about 15% w/w.

In an embodiment, the at least one diluent comprises about 10-40% w/w of water, such as about 10-35% w/w or 15-30% w/w, for example, about 15, about 16, about 17, about 18, about 19, about 20, about 21, about 22, about 23, about 24, about 25, about 26, about 27, about 28, about 29, or about 30% w/w.

In an embodiment, the at least one diluent is a mixture of glycerin, ethanol, and water. In an embodiment, the at least one diluent is a mixture of about 5-75% w/w of glycerin; about 1-20% w/w of ethanol; and about 10-40% w/w of water. In an embodiment, the at least one diluent is a mixture of about 30-50% w/w of glycerin, about 5-15% w/w of ethanol, and about 15-35% w/w of water. In an embodiment, the at least one diluent is a mixture of about 20-30% w/w of glycerin, about 5-15% w/w of ethanol, and about 15-35% w/w of water. In an embodiment, the at least one diluent is a mixture of about 40% w/w of glycerin, about 9-10% w/w of ethanol, and about 20-25% w/w of water.

In an embodiment, the topical gel composition further comprises a local anesthetic such as lidocaine or anti-inflammatory agent such as COX, COX-1 or COX-2 inhibitors or their mixtures.

In an embodiment, the topical gel composition further may comprise at least one or more additional ingredients or excipients selected from antioxidants, alkalizers or alkalizing agents, buffering agents, moisturizing agents, humectants, surfactants, neutralizing agents, chelating agents, and emollients. In an embodiment, the topical gel composition further may comprise at least one or more additional ingredients or excipients selected from buffering agents, moisturizing agents, humectants, surfactants, neutralizing agents, chelating agents, and emollients.

In an embodiment, the topical pharmaceutical gel composition further comprises at least one antioxidant. In an embodiment, the at least one antioxidant is chosen from edetate disodium, sodium sulphite, sodium metabisulfite, propyl gallate, edetate trisodium, tocopherol derivatives, butylated hydroxyl toluene, butylated hydroxyl anisole, ascorbic acid, fumaric acid, malic acid, citric acid, and mixtures thereof.

In an embodiment, the at least one antioxidant is present in an amount equal to or less than 5% w/w. In an embodiment, the pharmaceutical gel composition does not include at least one antioxidant.

In an embodiment, the topical pharmaceutical gel composition further comprises at least one alkalizer or alkanizing agent.

In an embodiment, the at least one alkalizer or alkanizing agent include organic and inorganic basic compounds. Examples of inorganic basic salts include ammonium hydroxide, alkali metal salts, and alkaline earth metal salts such as magnesium oxide, magnesium hydroxide, calcium hydroxide, sodium hydroxide, potassium hydroxide, lithium hydroxide, aluminum hydroxide, potassium carbonate, sodium bicarbonate and combinations thereof.

In an embodiment, the alkalizer or alkanizing agent is aqueous sodium hydroxide solution.

In an embodiment, the topical pharmaceutical gel compositions further comprise or are co-administered with steroids such as prednisolone, busenonide or hydrocortisone, anesthetics such as acetylsalicylic acid, locally acting lignocaine, and soothants.

In an embodiment, the topical pharmaceutical gel compositions further comprise typical components used in existing fissure or hemorrhoidal treatment, such as zinc oxide, benzyl benzoate, bismuth oxide, bismuth subgallate or Peru balsam.

In one aspect, the topical pharmaceutical gel composition comprises an amlodipine salt, hydroxyethyl cellulose, methyl parahydroxybenzoate, ethanol, water, propylene glycol, and glycerin with the amlodipine salt present at a concentration chosen from about 1 w/w, about 0.5% w/w, about 0.2% w/w, about 0.1% w/w, about 0.05% w/w and 0.01% w/w, as measured as the free base.

In one aspect, the topical pharmaceutical gel composition consists essentially of amlodipine salt, hydroxyethyl cellulose, methyl parahydroxybenzoate, ethanol, water, propylene glycol, and glycerin with the amlodipine salt present at a concentration chosen from about 1% w/w, about 0.5% w/w, about 0.2% w/w, about 0.1% w/w, about 0.05% w/w and 0.01% w/w, as measured as the free base.

Also provided is a topical pharmaceutical gel composition of an amlodipine salt comprising:
  about 0.01-1% w/w of an amlodipine salt, as measured as the free base;
  about 5-75 w/w of at least one glycol solvent;
  about 0.1-10% w/w of at least one gelling agent;
  about 0.001-5% w/w of at least one preservative;
  about 5-75% w/w of glycerin;
  about 1-20% w/w of ethanol; and
  about 10-40% w/w of water.

Also provided is a topical pharmaceutical gel composition of an amlodipine salt comprising:
  about 0.01-1% w/w of an amlodipine besylate, as measured as the free base;
  about 5-75 w/w of at least one glycol solvent;
  about 0.1-10% w/w of at least one gelling agent;
  about 0.001-5% w/w of at least one preservative;
  about 5-75% w/w of glycerin;
  about 1-20% w/w of ethanol; and
  about 10-40% w/w of water.

Also provided is a topical pharmaceutical gel composition of an amlodipine salt comprising:
  about 0.01-1% w/w of an amlodipine salt, as measured as the free base;
  about 5-75 w/w of propylene glycol;
  about 0.1-10% w/w of at least one gelling agent;
  about 5-75% w/w of glycerin;
  about 1-20% w/w of ethanol; and
  about 10-40% w/w of water.

Also provided is a topical pharmaceutical gel composition of an amlodipine salt comprising:
  about 0.01-1% w/w of amlodipine besylate, as measured as the free base;
  about 5-75 w/w of propylene glycol;
  about 0.1-10% w/w of at least one gelling agent;
  about 5-75% w/w of glycerin;
  about 1-20% w/w of ethanol; and
  about 10-40% w/w of water.

Also provided is a topical pharmaceutical gel composition of an amlodipine salt comprising:
  about 0.01-1% w/w of an amlodipine salt, as measured as the free base;
  about 5-75 w/w of propylene glycol;
  about 0.1-10% w/w of hydroxyethyl cellulose, carbomers, carboxymethyl cellulose, or a mixture thereof;
  about 0.01-5% w/w of methyl parahydroxybenzoate;
  about 5-75% w/w of a glycerin;
  about 1-20% w/w of ethanol; and
  about 10-40% w/w of water.

Also provided is a topical pharmaceutical gel composition of an amlodipine salt comprising:
  about 0.01-1% w/w of an amlodipine besylate, as measured as the free base;
  about 5-75 w/w of propylene glycol;
  about 0.1-10% w/w of hydroxyethyl cellulose, carbomers, carboxymethyl cellulose, or a mixture thereof;
  about 0.01-5% w/w of methyl parahydroxybenzoate;
  about 5-75% w/w of a glycerin;
  about 1-20% w/w of ethanol; and
  about 10-40% w/w of water.

Also provided is a topical pharmaceutical gel composition of an amlodipine salt comprising:
  about 0.01-1% w/w of an amlodipine salt, as measured as the free base;
  about 5-75 w/w of propylene glycol;
  about 0.1-10% w/w of hydroxyethyl cellulose;
  about 0.01-5% w/w of methyl parahydroxybenzoate;
  about 5-75% w/w of a glycerin;
  about 1-20% w/w of ethanol; and
  about 10-40% w/w of water.

Also provided is a topical pharmaceutical gel composition of an amlodipine salt comprising:
  about 0.01-1% w/w of amlodipine besylate, as measured as the free base;
  about 5-75 w/w of propylene glycol;
  about 0.1-10% w/w of hydroxyethyl cellulose;
  about 0.01-5% w/w of methyl parahydroxybenzoate;
  about 5-75% w/w of glycerin;
  about 1-20% w/w of ethanol; and
  about 10-40% w/w of water.

Also provided is a topical pharmaceutical gel composition of an amlodipine salt comprising:
about 0.01-1% w/w of amlodipine salt, as measured as the free base;
about 5-75 w/w of at least one glycol solvent;
about 0.1-10% w/w of hydroxyethyl cellulose;
about 5-75% w/w of glycerin;
about 1-20% w/w of ethanol; and
about 10-40% w/w of water.

Also provided is a topical pharmaceutical gel composition of an amlodipine salt comprising:
about 0.01-1% w/w of amlodipine besylate, as measured as the free base;
about 5-75 w/w of at least one glycol solvent;
about 0.1-10% w/w of hydroxyethyl cellulose;
about 5-75% w/w of glycerin;
about 1-20% w/w of ethanol; and
about 10-40% w/w of water.

In an embodiment, the topical pharmaceutical gel formulation of an amlodipine salt is storage stable at room temperature for a period of at least 24 months with 95-105% assay criterion limit.

In an embodiment, the topical pharmaceutical gel formulation of an amlodipine salt is storage stable at a temperature of 2-8° C. for a period of at least 24 months with 95-105% assay criterion limit.

In another aspect, degradation impurities (related substances) of an amlodipine salt in the topical pharmaceutical gel formulation is less than about 2.5% for a storage period of at least 24 months at room temperature.

In another aspect, degradation impurities (related substances) of an amlodipine salt in the topical pharmaceutical gel formulation is less than about 2.5% for a storage period of at least 24 months at a temperature of about 2-8° C.

In another aspect, relative bioavailability of topically applied amlodipine salt in the topical pharmaceutical gel formulation is less than 10% compared to oral administration. The topical administration of the pharmaceutical gel formulation for 28 days resulted in no local tolerance of histopathological findings.

In an embodiment, the shear viscosity of the topical pharmaceutical gel composition is in the range of about 5 to 30 Pas measured at 10 s$^{-1}$ shear rate by Kinexus Pro rheometer (Malvern Instruments Ltd.).

In an embodiment, the pH of the topical pharmaceutical gel composition is in the range of about 4.0-8.0.

In an embodiment, the density of the topical pharmaceutical gel composition is in the range of about 0.9-1.5 g/ml.

In an embodiment, the topical pharmaceutical gel composition is formulated as ointments, creams, suspensions, lotions, powders, solutions, pastes, gels, sprays, foam, oils, aerosols, suppositories or enemas.

In an embodiment, the topical pharmaceutical gel composition is applied to the affected areas of the skin to a patient suffering from anorectal diseases such as hemorrhoids, anal fissure and painful conditions after anorectal surgery.

Disclosed herein are topical pharmaceutical gel compositions for use in treating anorectal diseases such as hemorrhoids, anal fissure (acute and chronic), painful conditions after anorectal surgery, perianal abscess, prolapsed thrombosed piles, perianal haematoma, cancer invading the sphincters (anorectal cancer), anal herpes, anal warts, anal itching, proctalgia fugax, constipation, anal bleeding and Crohn's disease or another inflammatory bowel disease related anorectal disorders.

Also provided is a method for the treatment of an anorectal disease comprising topically applying a topical pharmaceutical gel composition of any one of claims 1 to 15 to a skin surface of a patient in need thereof.

In an embodiment, the anorectal disease is chosen from hemorrhoids, anal fissure (acute and chronic), painful conditions after anorectal surgery, perianal abscess, prolapsed thrombosed piles, perianal haematoma, cancer invading the sphincters (anorectal cancer), anal herpes, anal warts, anal itching, proctalgia fugax, constipation, anal bleeding and Crohn's disease or another inflammatory bowel disease related anorectal disorders.

Also disclosed herein is a method for the manufacture of topical gel formulation of an amlodipine salt. The method of manufacture comprises the following steps:
stirring the at least one diluent, the at least one glycol solvent, the amlodipine salt, the at least one preservative and the at least one gelling agent to form a gel; and
adding water up to the total weight/volume desired.

In an embodiment, the method of manufacture comprises the following steps:
mixing and homogenizing ethanol, glycol solvent and water;
dissolving an amlodipine salt and preservative in ethanol, glycol solvent and water;
adding the gelling agent to the dissolved solution;
mixing and homogenizing the solution to obtain a gel;
adding glycerin to the gel under continuous stirring;
adding water up to the total weight/volume desired.

In an embodiment, the method for the manufacture of a topical gel formulation of an amlodipine salt comprises the following steps:
mixing and homogenizing ethanol, glycol solvent and water;
dissolving an amlodipine salt and methyl parahydroxybenzoate in ethanol, glycol solvent and water;
adding hydroxyethyl cellulose to the completely dissolved (b) solution;
mixing and homogenizing the solution to obtain a gel;
adding glycerin to the gel under continuous stirring;
adding water up to the total weight/volume desired.

The examples, which follow, are not intended to be limiting of the scope of the present invention but read in conjunction with the detailed and general description above, provide further understanding of the present invention and an outline of a process for preparing the compositions of the invention.

EXAMPLES

Example 1

Preparation of Amlodipine Besylate Topical Pharmaceutical Gel Compositions Using Carbomer Amlodipine besylate topical pharmaceutical gel compositions were prepared using carbomer as gelling agent. Compositions of the prepared gels are summarized in Table 1.

TABLE 1

Topical pharmaceutical gel compositions prepared using carbomer

| | Sample No. | | |
|---|---|---|---|
| | #1 | #2 | #3 |
| | pH | | |
| | 7 | 6 | 5 |
| Component | Quantity (% w/w) | | |
| Amlodipine besylate | 0.100-0.200 | 0.100-0.200 | 0.100-0.200 |
| Carbomer (980 NF or 971 or Ultrez 10) | 1.000 | 1.010 | 0.950 |
| Ethanol | 5.910 | 4.950 | 5.510-5.610 |
| Methyl parahydroxybenzoate | 0.002 | 0.002 | 0.002 |
| Glycerin | 5.000 | 5.060 | 4.760 |
| Sodium hydroxide | 0.410 | 0.270 | 0.120 |
| Water | 87.470-87.570 | 88.500-88.600 | 88.460 |

Process of example #1: 0.2-0.4 g amlodipine besylate was dissolved in 9.8 g ethanol. 87.8-87.6 g water was added to the solution and mixed well. 2 g Carbomer was added to the prepared solution and stirred well until completely dissolved. Separately, 0.828 g sodium hydroxide was dissolved in 107.2 g water and 2 mL 0.2% methyl parahydroxibenzoate ethanolic solution was added. The two solutions were mixed together to form gel. 10 g glycerol was added to the gel and homogenized well.

Process of example #2: 0.2-0.4 g amlodipine-besylate was dissolved in 9.8 g ethanol. 87.8-87.6 g water was added to the solution and mixed well. 2 g Carbomer was added to the prepared solution and stirred well until completely dissolved. Separately, 0.540 g sodium hydroxide was dissolved in 107.5 g water and 2 mL 0.2% methyl parahydroxibenzoate ethanolic solution was added. The two solutions were mixed together to form gel. 10 g glycerol was added to the gel and homogenized well.

Process of example #3: 0.2 g Carbomer was dissolved in 100 g water. 0.25 g sodium hydroxide was dissolved in 86 g water. The two solutions were mixed together to form gel. 2 mL 0.2% methyl parahydroxibenzoate ethanolic solution, 10 g glycerol and 9.9-10 g 2-4% amlodipine-besylate ethanolic solution were added to the gel and homogenized well.

Example 2

Preparation of Amlodipine Besylate Topical Pharmaceutical Gel Compositions Using Carboxymethyl Cellulose Amlodipine besylate topical pharmaceutical gel compositions were prepared using carboxymethyl cellulose as gelling agent. Compositions of the prepared gels are summarized in Table 2.

TABLE 2

Topical pharmaceutical gel compositions prepared using carboxymethyl cellulose

| | Sample No. |
|---|---|
| | #4 |
| | pH |
| | 7 |
| Component | Quantity (% w/w) |
| Amlodipine besylate | 0.100-0.200 |
| Carboxymethyl cellulose | 2.090 |
| Ethanol | 6.150 |
| Methyl parahydroxybenzoate | 0.001 |
| Glycerin | 5.210 |
| Water | 86.3400-86.440 |

Process of example #4: 0.1-0.2 g amlodipine-besylate was dissolved in 4.9 g ethanol and then 5 g 0.2% methyl parahydroxibenzoate ethanolic solution and 87.8-87.9 g water was added to the solution. 2 g carboxymethyl cellulose was added to the solution to form a gel. 5 g glycerol was homogenized in the gel.

Example 3

Preparation of Amlodipine Besylate Topical Pharmaceutical Gel Compositions Using Hydroxyethyl Cellulose Amlodipine besylate topical pharmaceutical gel compositions were prepared using hydroxyethyl cellulose as gelling agent. Compositions of the prepared gels are summarized in Table 3.

TABLE 3

Topical pharmaceutical gel compositions prepared using hydroxyethyl cellulose

| | Sample No. | | |
|---|---|---|---|
| | #5 | #6 | #7 |
| | pH | | |
| | 7 | 7 | 7 |
| Component | Quantity (% w/w) | | |
| Amlodipine besylate | 0.10-0.20 | 0.14-0.28 | 0.14-0.28 |
| Hydroxyethyl cellulose | 2.00 | 2.00 | 2.00 |
| Ethanol | 5.91 | 10.86 | 9.60 |
| Methyl parahydroxybenzoate | 0.002 | 0.002 | 0.100 |
| Glycerin | 5.00 | 40.00 | 40.00 |
| Propylene glycol | 0 | 0 | 25.00 |
| Water | 86.89-86.99 | 46.86-47.00 | 23.02-23.16 |

Process of example 5: 0.2-0.4 g amlodipine-besylate was dissolved in 9.8 g ethanol and then 2 g 0.2% methyl parahydroxybenzoate ethanolic solution and 173.6-173.8 g water was added to the solution. 4 g hydroxyethyl cellulose was added to the prepared solution and mixed well to form a gel. 10 g glycerol was homogenized in the gel.

Process of example 6: 0.14-0.28 g amlodipine-besylate was dissolved in 9.86 g ethanol and then 1 g 0.2% methyl parahydroxybenzoate ethanolic solution and 46.95-47.00 g water was added to the solution. 2 g hydroxyethyl cellulose was added to the solution and mixed well to form a gel. 40 g glycerol was homogenized in the gel.

Process of example 7: 9.6 g ethanol, 25 g propylene glycol and 23.02-23.16 g water was mixed well. 0.14-0.28 g amlodipine-besylate and 0.1 g methyl parahydroxybenzoate was dissolved in the solvent mixture. 2 g hydroxyethyl cellulose was added to the solvent mixture and mixed well to form a gel. 40 g glycerol was homogenized in the gel.

Example 4

Preparation of Amlodipine Maleate and Amlodipine Mesylate Topical Pharmaceutical Gel Compositions Using Hydroxyethyl Cellulose Amlodipine maleate and amlodipine mesylate topical pharmaceutical gel compositions were prepared using hydroxyethyl cellulose as gelling agent. Compositions of the prepared gels are summarized in Table 4.

TABLE 4

Topical pharmaceutical gel compositions prepared using hydroxyethyl cellulose but different amlodipine salts, not amlodipine besylate

| | Sample No. | |
|---|---|---|
| | #8 | #9 |
| | pH | |
| | 7 | 7 |
| Component | Quantity (% w/w) | |
| Amlodipine maleate | 0.13-0.26 | 0 |
| Amlodipine mesylate | 0 | 0.12-0.25 |
| Hydroxyethyl cellulose | 2.00 | 2.00 |

TABLE 4-continued

Topical pharmaceutical gel compositions prepared using hydroxyethyl cellulose but different amlodipine salts, not amlodipine besylate

| | Sample No. | |
|---|---|---|
| | #8 | #9 |
| | pH | |
| | 7 | 7 |
| Component | Quantity (% w/w) | |
| Ethanol | 9.60 | 9.60 |
| Methyl parahydroxybenzoate | 0.004 | 0.004 |
| Glycerin | 40.00 | 40.00 |
| Propylene glycol | 25.00 | 25.00 |
| Water | 23.14-23.27 | 23.15-23.27 |

Process of example 8: 9.6 g ethanol, 25 g propylene glycol and 23.14-23.27 g water was mixed well. 0.13-0.26 g amlodipine-maleate and 0.004 g methyl parahydroxybenzoate was dissolved in the solvent mixture. 2 g hydroxyethyl cellulose was added to the solvent mixture and mixed well to form a gel. 40 g glycerol was homogenized in the gel.

Process of example 9: 9.6 g ethanol, 25 g propylene glycol and 23.15-23.27 g water was mixed well. 0.12-0,258 g amlodipine-mesylate and 0.004 g methyl parahydroxybenzoate was dissolved in the solvent mixture. 2 g hydroxyethyl cellulose was added to the solvent mixture and mixed well to form a gel. 40 g glycerol was homogenized in the gel.

Example 5

Amlodipine besylate topical pharmaceutical gel compositions prepared according to Example 1-4 were stored in a closed vial at RT and 4° C. in order to investigate the stability. At different time points related substances tests were performed by RP-HPLC method. Amlodipine besylate topical pharmaceutical gel compositions prepared using hydroxyethyl cellulose were more stable compared to the composition prepared using carbomer. Topical pharmaceutical gels of different amlodipine salts prepared using hydroxyethyl cellulose showed different decomposition profile after 1 month storage at 4° C. and RT. Only the amlodipine besylate gel prepared using hydroxyethyl cellulose had satisfying degradation profile in both storage conditions. (Table 5).

TABLE 5

Amlodipine decomposition in different topical pharmaceutical gel compositions in time. Amlodipine besylate content of sample #1-5 is 0.1%. Amlodipine content of sample #6-9 is 0.1%.

| | Degradation after storage at 4° C. (%) | | | | | Degradation after storage at RT (%) | | | | |
|---|---|---|---|---|---|---|---|---|---|---|
| Sample No. | 1 week | 2 weeks | 1 month | 2 months | 3 months | 1 week | 2 weeks | 1 month | 2 months | 3 months |
| #1 | — | — | 0.50 | — | 1.18 | — | — | 2.07 | — | 5.22 |
| #2 | — | — | 0.21 | — | 1.71 | — | — | 1.85 | — | 6.79 |
| #3 | 0.53 | — | — | — | — | 2.60 | — | — | — | — |
| #4 | — | 0.14 | — | — | — | — | 12.07 | — | — | — |
| #5 | — | — | 0.19 | 0.38 | — | — | — | 0.46 | 0.98 | — |
| #6 | — | — | 0.24 | — | — | — | — | 0.31 | — | — |
| #7 | — | — | 0.19 | — | 0.32 | — | — | 0.44 | — | 0.68 |
| #8 | — | — | 0.20 | — | — | — | — | 0.93 | — | — |
| #9 | — | — | 0.28 | — | — | — | — | 0.33 | — | — |

Example 6

In Vitro Permeability of Amlodipine Besylate Topical Pharmaceutical Gel Compositions In vitro permeability of amlodipine besylate, amlodipine mesylate and amlodipine maleate gels was investigated using dialysis measurement. The donor compartment contained 4000 mg topical pharmaceutical gel composition, while the receiver medium was phosphate buffer, pH 7.4 (100 ml). The measurement was performed at 37±0.5° C. The dialysis membrane was SnakeSkin Dialysis Tubing, 3.5K MWCO (35 mm dry I.D.). Amlodipine besylate topical pharmaceutical gel composition prepared using hydroxyethyl cellulose showed significantly higher in vitro permeability compared to the compositions prepared with different amlodipine salts or using carbomer as gelling agent. Amlodipine content of the receiver compartment was 1.7 times higher for the amlodipine besylate topical pharmaceutical gel compositions prepared using hydroxyethyl cellulose compared to other gels' (Table 6).

TABLE 6

In vitro permeability of amlodipine besylate, amlodipine mesylate and amlodipine maleate gels

| t (min) | Permeability of gel example #1 Dissolved API in receiver compartment (%) | Permeability of gel example #7 Dissolved API in receiver compartment (%) |
|---|---|---|
| 15 | 2.15 | 1.21 |
| 30 | 4.92 | 7.04 |
| 60 | 11.21 | 19.53 |
| 120 | 26.90 | 48.02 |
| 180 | 40.64 | 68.49 |
| 240 | 51.08 | 86.44 |

| t (min) | Permeability of gel example #8 Dissolved API in receiver compartment (%) | Permeability of gel example #9 Dissolved API in receiver compartment (%) |
|---|---|---|
| 15 | 0.77 | 0.54 |
| 30 | 3.25 | 2.75 |
| 60 | 10.19 | 9.35 |
| 120 | 29.29 | 28.78 |
| 180 | 42.00 | 40.47 |
| 240 | 56.11 | 52.64 | supernatant subjected to reverse phase chromatographic separation with gradient elution. Following electrospray ionization in positive mode the analyte was detected in MRM mode at the following transitions: Amlodipine: 409.10→238.15 m/z, IS: 413.10→238.15 m/z, Calibration range: 50 pg/mL-50 ng/mL, LLOQ: 50 pg/mL. Pharmacokinetic analysis was performed using a validated Phoenix WinNonlin® software version 6.3 (Pharsight Corporation, USA). The individual and mean plasma level versus time curves were evaluated using noncompartmental method. The results are shown in the FIGURE and Table 7. It was be concluded that 28-day repeated topical administration of 0.2% amlodipine gel resulted in very low total systemic exposure. At the end of the repeated administration all measured plasma concentrations remained below 300 pg/mL and both the average $C_{max}$ and $AUC_{0-24\,h}$ values were around than 5% of those obtained after repeated oral administration at the same dose.

TABLE 7

Pharmacokinetic parameters following oral administration of amlodipine tablets or topical administration of 0.2% topical pharmaceutical gel in female Göttingen minipigs.

| | Animal No. | #1 | #2 | #3 | #4 | Mean | S.D. |
|---|---|---|---|---|---|---|---|
| Oral, day 28, 2 mg/day | AUC | 36.3495 | 46.079 | 62.522 | 55.6115 | 50.1405 | 11.4006 |
| | $t_{max}$ | 4.0 | 4.0 | 6.0 | 4.0 | 4.5 | 1 |
| | $C_{max}$ | 2.39 | 3.48 | 3.52 | 4.05 | 3.36 | 0.6969 |
| Topical, day 28, 2 mg/day | AUC | 0.918 | 3.9941 | 3.744 | 1.015 | 2.417775 | 1.6794 |
| | $t_{max}$ | 36.0 | 0.0 | 4.0 | 4.0 | 4.0 | 16.7730 |
| | $C_{max}$ | 0.0765 | 0.265 | 0.276 | 0.0683 | 0.17145 | 0.1145 |

Example 7

28-Day Dermal Tolerance Study Followed by an 8-Day Recovery Period in Minipigs Methods The purpose of this study was to obtain information on the dermal local tolerance and dermal irritation of the 0.2% w/w amlodipine topical pharmaceutical gel composition in minipigs administered twice daily topically (dermal) over a period of 28 days and to assess reversibility of any effect after an 8-day recovery period. In addition, the pharmacokinetic profile of the systemic exposure was investigated.

Amlodipine gel or placebo was measured onto plastic spatulas and was homogenously smeared on the left and right treatment sites (treatment area: approx. 20 cm²). The application sites were non-occluded.

Pharmacokinetic investigation: Approx. 3 mL blood was collected into plastic vials containing K3-EDTA as anticoagulant at the following time points after last treatment: 0 min, 1 h, 2 h, 4 h, 6 h, 8 h, 12 h, 16 h, 24 h, 36 h and 48 h after treatment (11 samples/animal). Amlodipine was quantified in minipig plasma using a reliable LC-MS/MS method developed in ATRC. Deuterated analogue of amlodipine (Amlodipine-d4) served as internal standard (IS). The plasma proteins were precipitated with methanol and the Viability, mortality and clinical signs: Viability, mortality and clinical signs were recorded three times daily (once before and twice after the first treatment) on the treatment days and twice on the treatment-free days. No mortality occurred during the course of the study. No clinical signs were observed related to the amlodipine gel during the study.

Body weight: Measurement of body weight was performed twice during the acclimatization period and then on the treatment days before administration. There was no difference related to the test item in the body weight gain between the animals treated with placebo and amlodipine gel.

Local tolerance: The treated skin area of the animals (on both side) was observed twice daily during treatment (before treatments) and recovery periods in order to evaluate the local tolerance with special regard to erythema, edema, inflammation, hypersensitivity, infection, biofilm formation, ischemia, necrosis, erysipelas and cellulitis. No local tolerance findings related to amlodipine gel or placebo were observed on the treatment sites during the entire study Necropsy: At the end of the recovery period (on study day 37). No amlodipine gel or placebo related macroscopic findings were observed in any animals during necropsy.

Histopathology: Full histopathological examinations of samples from treatment sites from all animals. Treatment-related effects or toxicity was not seen following 28 days dermal exposition and 8 days recovery with placebo or amlodipine gel In conclusion the dermal tolerance study with twice daily topical (dermal) amlodipine gel at dose level of 2 mg/animal/treatment to minipigs over a period of 28 days resulted in no adverse effects. According to the results, the 2 mg/animal/treatment dose was well tolerated in all animals.

From the foregoing description, one skilled in the art can easily ascertain the essential characteristics of this invention, and without departing from the spirit and scope thereof, can make various changes and modifications of the invention to adapt it to various usages and conditions.

The invention claimed is:

1. A stable topical pharmaceutical gel composition of amlodipine besylate comprising:
   about 0.01-1% w/w of amlodipine besylate, as measured as the free base, wherein said amlodipine besylate is present in a dissolved state in said gel, and wherein the degradation impurities of said amlodipine besylate is less than about 2.5% for a storage period of at least 24 months at a temperature of about 2-8° C.;
   about 5-75% w/w of at least one glycol solvent;
   about 0.1-10% w/w of hydroxyethyl cellulose;
   about 30-50% w/w of glycerin;
   about 5-15% w/w of ethanol; and
   about 15-35% w/w of water.

2. The stable topical pharmaceutical gel composition according to claim 1, wherein said at least one glycol solvent is chosen from propylene glycol, polyethylene glycol, ethylene glycol, butylene glycol, hexylene glycol, and mixtures thereof.

3. The stable topical pharmaceutical gel composition according to claim 2, wherein said glycol solvent is propylene glycol.

4. The stable topical pharmaceutical gel composition according to claim 1, wherein said amlodipine besylate is present at a concentration of 0.01-1% w/w as measured as the free base, wherein said at least one glycol solvent is propylene glycol and is present at a concentration of 5-75% w/w, wherein said hydroxyethyl cellulose is present at a concentration of 0.1-10% w/w, wherein said glycerin is present at a concentration of 30-50% w/w, wherein said ethanol is present at a concentration of 5-15% w/w, wherein said water is present at a concentration of 15-35% w/w, wherein said stable topical pharmaceutical gel composition further comprises methyl parahydroxybenzoate, and wherein said methyl parahydroxybenzoate is present at a concentration of 0.01-5% w/w.

5. The stable topical pharmaceutical gel composition according to claim 1, wherein said amlodipine besylate is present at a concentration of about 0.1-1% w/w, as measured as the free base.

6. The stable topical pharmaceutical gel composition according to claim 4, wherein the degradation impurities of said amlodipine besylate is less than 2.5% for a storage period of at least 24 months at a temperature of about 2-8° C.

* * * * *

UNITED STATES PATENT AND TRADEMARK OFFICE
CERTIFICATE OF CORRECTION

PATENT NO. : 11,197,848 B2
APPLICATION NO. : 16/425028
DATED : December 14, 2021
INVENTOR(S) : László Ritter et al.

Page 1 of 1

It is certified that error appears in the above-identified patent and that said Letters Patent is hereby corrected as shown below:

In the Specification

Column 9,
Line 19, "about 5-75 w/w" should read --about 5-75% w/w--.

Column 11,
Line 60, "about 5-75 w/w" should read --about 5-75% w/w--.

Column 12,
Line 3, "about 5-75 w/w" should read --about 5-75% w/w--.
Line 12, "about 5-75 w/w" should read --about 5-75% w/w--.
Line 21, "about 5-75 w/w" should read --about 5-75% w/w--.
Line 30, "about 5-75 w/w" should read --about 5-75% w/w--.
Line 41, "about 5-75 w/w" should read --about 5-75% w/w--.
Line 52, "about 5-75 w/w" should read --about 5-75% w/w--.
Line 62, "about 5-75 w/w" should read --about 5-75% w/w--.

Column 13,
Line 5, "about 5-75 w/w" should read --about 5-75% w/w--.
Line 15, "about 5-75 w/w" should read --about 5-75% w/w--.

Signed and Sealed this
Fifth Day of July, 2022

Katherine Kelly Vidal
*Director of the United States Patent and Trademark Office*